United States Patent [19]

Garcia et al.

[11] Patent Number: 5,391,751
[45] Date of Patent: * Feb. 21, 1995

[54] 2,2-DIMETHYLCHROMENE DERIVATIVES, PROCESS FOR THEIR PREPARATION AND PHARMACEUTICAL COMPOSITIONS IN WHICH THEY ARE PRESENT

[76] Inventors: Georges Garcia, 27, rue des Aires; Alain Di Malta, 170, rue de Vigne Belle - St Clement-la-Riviere, both of 34908 Saint-Gely-du-Fesc; Patrick Gautier, Lieu dit Manavieille, 34660 Cournonterral, all of France

[ * ] Notice: The portion of the term of this patent subsequent to Feb. 8, 2011 has been disclaimed.

[21] Appl. No.: 746,974

[22] Filed: Aug. 19, 1991

Related U.S. Application Data

[63] Continuation of Ser. No. 255,605, Oct. 11, 1988, abandoned.

[30] Foreign Application Priority Data

Oct. 12, 1987 [FR] France .................. 87 14067

[51] Int. Cl.6 .................................. C07D 405/04
[52] U.S. Cl. .................. 514/337; 546/269; 546/24
[58] Field of Search ............ 546/269, 24; 514/337

[56] References Cited

U.S. PATENT DOCUMENTS 4,782,083 11/1988 Cassidy et al. ............. 514/456

OTHER PUBLICATIONS

Haeusler et al. CA 109:230806r, 1988.

Arch et al., *Br. J. Pharmacol.*, 95, 763–770, 1988.
Steinberg et al., *Chemtech*, 436–438, Jul. 1990.
Allen et al., *Br. J. Pharmac.*, 89, 395–405, 1986.

*Primary Examiner*—Jane T. Fan
*Attorney, Agent, or Firm*—Bacon & Thomas

[57] ABSTRACT

The present invention relates to 2,2-dimethylchromene derivatives of the formula:

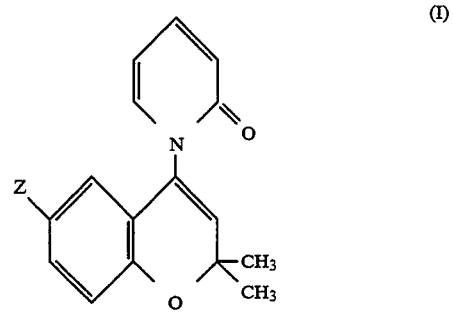

in which Z represents a halogen atom or a cyano, nitro, acetyl, phosphono or dialkoxyphosohoryl group, the alkoxy group containing 1 to 3 carbon atoms, and the pharmaceutically acceptable salts of the phosphono group.

These compounds show an antihypertensive and antiarrythmic activity.

The present invention also relates to a process for the preparation of said compounds and to the pharmaceutical compositions in which the are present.

9 Claims, No Drawings

2,2-DIMETHYLCHROMENE DERIVATIVES, PROCESS FOR THEIR PREPARATION AND PHARMACEUTICAL COMPOSITIONS IN WHICH THEY ARE PRESENT

This application is a continuation of application Ser. No. 07/255,605, filed Oct. 11, 1988, now abandoned.

The present invention relates to chromene derivatives having an antihypertensive and antiarrythmic activity. It also relates to a process for their preparation and pharmaceutical compositions in which they are present.

Belgian Patent 829 611 mentions a whole series of chroman-3-ol derivatives having an antihypertensive activity; these derivatives are characterized by the presence of a group $NR_1R_2$ in the 4-position, in which is hydrogen or an optionally substituted hydrocarbon group and $R_2$ is hydrogen or an alkyl, it being possible for $NR_1R_2$ to be a heterocyclic group containing from 3 to 8 atoms, which is unsubstituted or substituted by one or two methyl groups, and by the presence, in some cases, of a large number of possible substituents in the 6-position or 7-position.

European patent application published under number 76 075 describes chroman-3-ol derivatives having an antihypertensive activity which are characterized by the presence of a 2-oxopyrrolidin-1-yl group or a 2-oxopiperidino group in the 4-position and by the presence, in some cases, of numerous possible substituents, including the cyano group, in the 6-position or 7-position.

European patent application 93535 describes 2,2-dimethylchromene derivatives which are characterized by the presence of a 2-oxopiperidino or 2-oxopyrrolidin-1-yl group in the 4-position and by the presence, in some cases, of numerous possible substituents in the 6-position or 7-position.

Furthermore, an article published in J. Med. Chem., 1986, 29, 2194–2201, compares the antihypertensive activities of the chromanol derivatives and corresponding chromene derivatives described in the 2 European patent applications mentioned above.

The results obtained for the decrease in the blood pressure of spontaneously hypertensive rats show that the chromanol derivatives have similar activities to the corresponding chromene derivatives.

It has now been found that 2,2-dimethylchromene derivatives which are characterized by the presence of a 2-oxo-1,2-dihydropyrid-1-yl group in the 4-position possess an excellent antihypertensive and antiarrhythmic activity and a very low toxicity.

Totally surprisingly, it has been found that the antihypertensive activity of the derivatives according to the present invention is greater than that of the corresponding chroman-3-ol derivatives.

Thus, according to one of its aspects, the present invention relates to 2,2-dimethylchromene derivatives of the formula

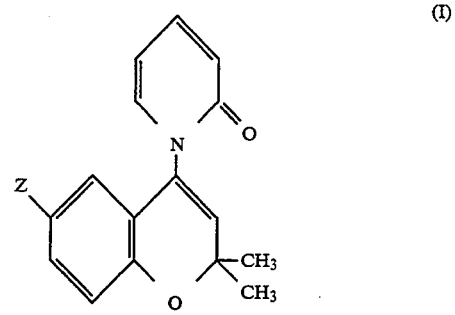

(I)

in which Z represents a halogen atom or a cyano, nitro, acetyl, phosphono or dialkoxyphosphoryl group, the alkoxy group containing 1 to 3 carbon atoms, and to the pharmaceutically acceptable salts of the phosphono group.

The pharmaceutically acceptable salts are preferably those of alkali metals and alkaline earth metals, such as the sodium and potassium salts, or these of organic bases such as triethanolamine, trometamol, ethanolamine, N-methylpiperidine or tert-butylamine.

The preferred halogen atoms are chlorine and bromine.

The present invention further relates to a process for the preparation of the compounds (I).

The said process comprises dehydrating the chroman-3-ol of the formula

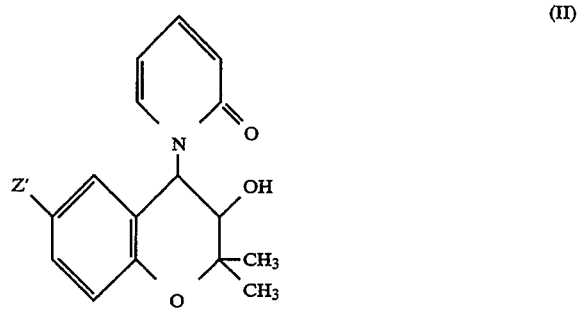

(II)

in which Z' represents a halogen atom or a cyano, nitro, acetyl or dialkoxyphosphoryl group, and, if desired, converting the dialkoxyphosphoryl group into the phosphono group, and then, if desired, converting the resulting phosphonic acid into its pharmaceutically acceptable salts. The final reaction product (I) is isolated by the conventional methods.

When Z' represents a dialkoxyphosphoryl group, this can be converted into the corresponding group by transesterification with a trimethylsilyl halide, preferably the bromide, and hydrolysis di(trimethylsilyl ester) simply by reaction with water. This gives a compound of formula I in which Z represents a phosphono group and the said compound can be converts into one Of its pharmaceutically acceptable salts, for example those of alkali metals or alkaline earth metals, such as the sodium or potassium salts, or those of organic bases such as triethanolamine, trometamol, ethanolamine, tert-butylamine or N-methylpiperidine.

Dehydration of the chroman-3-ol is effected with an alkali metal hydride such as sodium hydride, in an inert solvent such as tetrahydrofuran, at a temperature of between 50° C. and 100° C.

To prepare the chroman-3-ol (II), a chromane epoxide of the formula

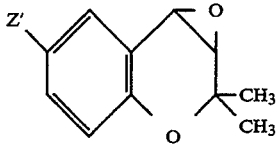
(III)

in which Z' is as defined above, is treated with 2-hydroxypyridine.

The reaction for opening the epoxide III is carried out at a temperature of between 10° and 100° C. in an inert organic solvent such as dioxane, tetrahydrofuran, methyl tert-butyl ether, dimethyl sulfoxide or dimethylformamide, in the presence of a basic condensation agent such as sodium hydride or a quaternary ammonium hydroxide like benzyltrimethylammonium hydroxide. Under these operating conditions, opening of the epoxide III leads to a chroman-3-ol derivative in the trans configuration.

The starting epoxides of formula III are known or prepared by known methods. Thus the epoxide III in which Z' represents the cyano group is described in Belgian patent 852 955; the epoxides III in which Z' represents the nitro group or an acetyl group are described in J. Med. Chem., 1983, 26, 1582–1589; the epoxides III in which Z' represents a halogen are prepared according to Tetrahedron, 1981, 37, (15), 2613–2616.

The starting epoxides of formula III in which Z' represents a dialkoxyphosphoryl group are not described in the literature. They can be prepared from 6-bromo-2,2-dimethylchromene (J. Chem. Soc., 1960, 3094–3098) of the formula

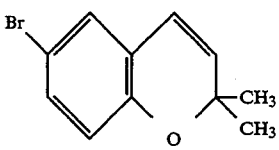
(IV)

by reaction with a trialkyl phosphite in the presence of nickel chloride at 180° C. and by reaction of the resulting compound of the formula

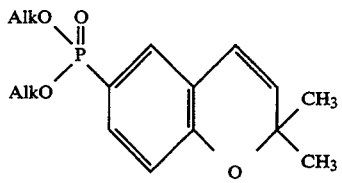
(V)

in which Alk represents an alkyl containing from 1 to 3 carbon atoms, with N-bromosuccinimide in aqueous dimethyl sulfoxide.

The resulting bromohydrin of the formula

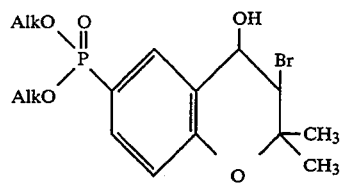
(VI)

in which Alk is as defined above, is then treated with an alkaline agent in a water/organic solvent mixture, for example water/dioxane, preferably at room temperature for a period of 8 to 20 hours, and the resulting epoxide of formula II in which Z' is a dialkoxyphosphoryl group is isolated by the conventional methods, for example by concentration of the reaction mixture and recovery of the residue with a solvent which removes the impurities, such as methylene chloride, washing with water and concentration.

The compounds of formula I increase the polarization of the smooth muscle fibers and have a vasodilative effect on the portal vein; their antihypertensive effect has been observed in animals.

Furthermore, it has been observed that the compounds according to the invention accelerate the repolarization of myocardial cells; their antiarrhythmic effect has been observed in parallel on an animal model.

No signs of toxicity are observed with these compounds at the pharmacologically active doses.

Thus the compounds according to the invention can be used in the treatment of hypertension and pathological disorders associated with contractions of the smooth muscle fibers of the gastrointestinal, respiratory, uterine and urinary systems, for example ulcers, asthma, premature uterine contraction and incontinence, and in the treatment of other cardiovascular pathological disorders such as angor, cardiac insufficiency and cerebral and peripheral vascular diseases. Furthermore, the compounds according to the invention can be used in the treatment of cardiac arrhythmia. Finally, the compounds of the present invention can be used for the topical treatment of alopecia.

The present invention further relates to pharmaceutical compositions containing an effective dose of a compound according to the invention, with suitable excipients. The said excipients are chosen according to the desired pharmaceutical form and the desired mode of administration.

In the pharmaceutical compositions of the present invention for oral, sublingual, subcutaneous, intramuscular, intravenous, topical, percutaneous or rectal administration, the active principles of formula I above, or their salts if appropriate, can be administered to animals and humans in unit forms of administration, mixed with conventional pharmaceutical carriers, for the prophylaxis or treatment of the above disorders or diseases. The appropriate unit forms of administration include oral forms such as tablets, gelatin capsules, powders, granules and solutions or suspensions to be taken orally, sublingual and buccal forms, subcutaneous, intramuscular or intravenous forms and rectal forms. For topical application, the compositions according to the invention can be used in creams, ointments or lotions.

To achieve the desired prophylactic or therapeutic effect, the daily dose of active principle can vary between 0.01 and 5 mg per kg of body weight.

Each unit dose can contain from 0.5 to 200 mg, preferably from 1 to 50 mg, of active ingredients combined with a pharmaceutical carrier. This unit dose can be administered 1 to 5 times a day so as to administer a daily dosage of 0.5 to 1000 mg, preferably 5 to 250 mg.

When a solid composition is prepared in the form of tablets, the main active principle is mixed with a pharmaceutical vehicle such as gelatin, starch, lactose, magnesium stearate, talc, gum arabic or the like. The tablets can be coated with sucrose or other appropriate substances or they can be treated so as to have a sustained or delayed activity and so as to release a predetermined amount of active principle continuously.

A preparation in the form of gelatin capsules is obtained by mixing the active ingredient with a diluent and pouring the mixture obtained into soft or hard gelatin capsules.

A preparation in the form of a syrup or elixir or for administration in the form of drops can contain the active principle together with a sweetener, which is preferably calorie-free, methylparaben and propylparaben as antiseptics, an agent for imparting taste and an appropriate colorant.

Water-dispersible granules or powders can contain the active principle mixed with dispersants or wetting agents, or suspending agents such as polyvinylpyrrolidone, as well as with sweeteners or taste correctors.

For rectal administration, suppositories are used which are prepared with binders melting at rectal temperature, for example cacao butter or polyethylene glycols.

For parenteral administration, aqueous suspensions, isotonic saline solutions or injectable sterile solutions are used which contain pharmacologically compatible dispersants and/or wetting agents, for example propylene glycol or butylene glycol.

The active principle can also be formulated as microcapsules, if appropriate with one or more carriers or additives.

The compositions of the present invention can contain, in addition to the products of formula I above or one of their pharmaceutically acceptable salts, other active principles such as, for example, tranquilizers or other drugs which can be useful in the treatment of the disorders or diseases indicated above.

The following Examples illustrate the invention without however implying a limitation. In the Examples as well as in the descriptive part and in the claims, the products are denoted as chromane derivatives. It is understood that the products of the present invention are 2,2-dimethyl-2H-chromene derivatives and that the terms "chromene" and "chromane" denote "2H-chromene" and "3,4-dihydro-2H-chromene" respectively.

PREPARATION OF
6-DIETHYLPHOSPHONO-2,2-DIMETHYL-3,4-EPOXYCHROMANE

A) 6-Diethylphosphono-2,2-dimethyl-2H-chromene 16 g of 6-bromo-2,2-dimethyl-2H-chromene are dissolved in 100 ml of triethyl phosphite. 2 g of nickel chloride are added and the mixture is refluxed at 180° C. for 24 hours in an autoclave. After the remaining triethyl phosphite has been concentrated, the expected product distills at 130°–140° C. under 0.1 mm Hg. 11.5 g are collected.

B)
trans-3-Bromo-6-diethylphosphono-2,2-dimethylchroman-4-ol 11 g of the previous product are dissolved in 62 ml of dimethyl sulfoxide containing 1.35 ml of water. 12.2 g of N-bromosuccinimide are added in small portions while the solution is kept at a temperature below 20° C. The mixture is stirred at room temperature for 30 minutes, 100 ml of water are then added and extraction is carried out with ethyl acetate. After drying over sodium sulfate, the organic phase is concentrated, the residue is taken up with 100 ml of acetone and 50 ml of water and the mixture is then refluxed for 5 hours. The acetone is concentrated, the residue is extracted with ether and the extract is dried over sodium sulfate and concentrated. The expected product crystallizes from isopropyl ether. After the crystals have been filtered off and dried, 3.2 g of product are collected.

Melting point: 124° C.

C)
6-Diethylphosphono-2,2-dimethyl-3,4-epoxychromane 23 g of the compound obtained in the previous step are mixed with 12 g of sodium hydroxide in 900 ml of dioxane and ]00 ml of water. After 24 hours at room temperature, the dioxane is concentrated, the residue is taken up with water and extracted with ethyl ether and the extract is then dried over sodium sulfate. After concentration, 16.2 g of the expected product are obtained.

EXAMPLE 1

6-Cyano-4-(1,2-dihydro-2-oxopyrid-1-yl)-2,2-dimethylchromene: SR 44866

A)
trans-6-Cyano-4-(1,2-dihydro-2-oxopyrid-1-yl)-2,2-dimethylchroman-3-ol 1 g of 6-cyano-2,2-dimethyl-3,4-epoxychromane is refluxed for 40 hours with 1 g of 2-hydroxypyridine in 10 ml of dioxane, in the presence of 0.20 ml of a methanolic solution containing 35% of benzyltrimethylammonium hydroxide. The mixture is taken up with 30 ml of water and the precipitate obtained is filtered off, washed with isopropyl ether and then recrystallized from 20 ml of absolute ethyl alcohol to give 0.9 g of the expected product.

Melting point: 243° C. with decomposition (capillary tube)

B) SR 44866

A mixture containing 1.7 g of the product obtained in step A and 150 mg of sodium hydride in 50 ml of tetrahydrofuran is refluxed for 2 hours. The tetrahydrofuran is evaporated off under vacuum, the residue is taken up with iced water and extraction is then carried out with ethyl acetate. The organic phase dried over sodium sulfate and then evaporated under vacuum. The residue is taken up in an isopropyl ether/ ethyl ether mixture (50/50, v/v). After filtration, washing with isopropyl ether and drying at 100° C. under vacuum, 800 mg of the expected product are collected.

Melting point: 151° C.

EXAMPLE 2

6-Diethylphosphono-4-(1,2-dihydro-2-oxopyrid-1-yl)-2,2-dimethylchromene: SR 45014

A)
trans-6-Diethylphosphono-4-(1,2-dihydro-2-oxopyrid-1-yl)-2,2-dimethylchroman-3-ol A mixture containing 5.6 g of 6-diethylphosphono-2,2-dimethyl-3,4-epoxychromane, 2.5 g of 2-hydroxypyridine and 4 drops of benzyltrimethylammonium hydroxide is refluxed for 48 hours. After the dioxane has been concentrated, the residue is taken up in methylene chloride and the mixture is washed twice with water and then dried over sodium sulfate and concentrated to dryness. Ethyl ether is added and the product crystallizes. After recrystallization from ethyl acetate, 1.5 g of the expected product are obtained. Melting point: 130° C. (capillary tube)

B) SR 45014

2 g of the chroman-3-ol obtained in the previous step are dissolved in 100 ml of tetrahydrofuran. 120 mg of sodium hydride are added in small portions and the mixture is then refluxed for 8 hours. After the reaction medium has been concentrated to dryness, the residue is extracted 3 times with methylene chloride. The organic phase is dried and concentrated and the oil obtained is purified by chromatography on a silica column using a methylene chloride/methanol mixture (98/2, v/v) as the eluent. This gives 200 mg of a waxy product characterized by its NMR spectrum and its IR spectrum.

The IR spectrum is run on a 2% solution of the product in methylene chloride: 980 cm$^{-1}$ (C—O—C), 1030 cm$^{-1}$ and 1055 cm$^{-1}$ (P—O—C), 1240 cm$^{-1}$ (P=O), 1490 cm$^{-1}$, 1540 cm$^{-1}$ and 1600 cm$^{-1}$ (C=C), 1670 cm$^{-1}$ (C=O), 2960 cm$^{-1}$, 2970 cm$^{-1}$ and 2990 cm$^{-1}$ (C—H).

The NMR spectrum is run at 250 MHz on a solution in DMSO.

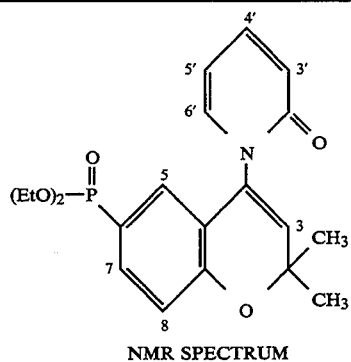

NMR SPECTRUM

| Delta | Appearance | Protons | Assignment |
|---|---|---|---|
| 1.1 ppm | T of D<br>JCH₃, CH₂ = 8 Hz<br>JCH₃, P = 2 Hz | 6H | 2CH₃ (Et) |
| 1.45 and 1.5 ppm | 2S | 6H | (CH₃)₂C |
| 3.83 ppm | M | 4H | 2CH₂ (Et) |
| 6.05 ppm | S | 1H | H3 |
| 6.3 ppm | T of D<br>Jo5', 6' = 7 Hz<br>Jm5', 3' = 1.25 Hz | 1H | H5' |
| 6.45 ppm | D of D<br>Jo3', 4' = 10 Hz<br>Jm3', 5' = 1.25 Hz | 1H | H3' |

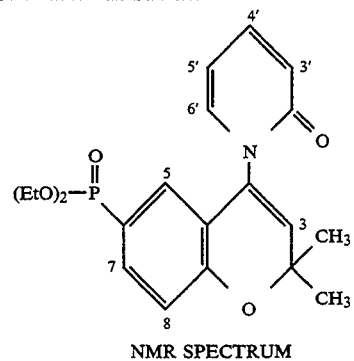

NMR SPECTRUM

| Delta | Appearance | Protons | Assignment |
|---|---|---|---|
| 6.77 ppm | D of D<br>J5, P = 13 Hz<br>J5, 7 = 1.5 Hz | 1H | H5 |
| 6.95 ppm | D of D<br>Jo8, 7 = 8 Hz<br>J8, P = 3 Hz | 1H | H8 |
| 7.45 ppm | D of D of D<br>J7, P = 13 Hz<br>Jo7, 8 = 8 Hz<br>Jm7, 5 = 1.5 Hz | 1H | H7 |
| 7.53 ppm | T of D<br>Jo4', 3' = 7 Hz<br>Jo4', 5' = 7 Hz<br>Jm4', 6' = 1.8 Hz | 1H | H4' |
| 7.56 ppm | D<br>Jo6', 5' = 7 Hz | 1H | H6' |

S denotes Singlet
D denotes Doublet
T denotes Triplet
M denotes Multiplet
J represents the coupling constant

EXAMPLE 3

6-Bromo-4-(1,2-dihydro-2-oxopyrid-1-yl)-2,2dimethyl-chromene: SR 45374

A) 6-Bromo-2,2-dimethyl-3,4-epoxychromane

A solution containing 6 g of 6-bromo-2,2-dimethylchromene, 20 ml of DMSO and 5 ml of water is prepared. 5 g of N-bromosuccinimide are added in small portions at a temperature below 10° C. and the mixture is stirred for 1 hour. 100 ml of water are added, extraction is then carried out twice with methylene chloride and the organic phase is washed with water, dried over sodium sulfate and concentrated to give 5.4 g of 3,6-dibromo-2,2-dimethyl-4-hydroxychromane.

The previous compound is dissolved in 200 ml of dioxane. 20 ml of a 10% solution of sodium hydroxide are added and the mixture is stirred for 12 hours at room temperature. The dioxane is concentrated, the residue is then taken up with 100 ml of methylene chloride and the organic phase is washed twice with water, dried over sodium sulfate and concentrated. The oil obtained is chromatographed on a silica column using a hexane/ethyl acetate mixture (98/2) as the eluent. This gives 2.2 g of the expected epoxide.

B)
trans-6-Bromo-4-(1,2-dihydro-2-oxopyrid-1-yl)-2,2-dimethylchroman-3-ol

The compound obtained in the previous step is dissolved in 20 ml of THF, 1.5 g of 2-hydroxypyridine and 0.2 ml of benzyltrimethylammonium hydroxide are added and the mixture is then refluxed for 24 hours. It is dried over sodium sulfate and concentrated. The product crystallizes from isopropyl ether to give 1.5 g of the expected product.

Melting point: 248° C.

C) SR 45374

70 mg of sodium hydride are added in small portions to a solution of 1 g of the product prepared in the previous step, in 20 ml of tetrahydrofuran, and the mixture is refluxed for 6 hours. It is concentrated to dryness and the residue is then taken up with ethyl ether and washed twice with water. The ether phase is dried over sodium sulfate and concentrated. The product crystallizes from an isopropyl ether/hexane mixture (50/50) to give 680 mg of the expected product.

Melting point: 120° C.
Yield: 40.2%

EXAMPLE 4

6-Chloro-4-(1,2-dihydro-2-oxopyrid-1-yl)-2,2dimethyl-chromene: SR 45435

A)
trans-6-Chloro-4-(1,2-dihydro-2-oxopyrid-1-yl)-2,2-dimethylchroman-3-ol

Following the procedure of Example 3, 6-chloro-2,2-dimethyl-3,4-epoxychromane is prepared and reacted with 2-hydroxypyridine to give the expected product.
Melting point: 250° C.

B) SR 45435

A mixture containing 500 mg of the product obtained in the previous step, 20 ml of tetrahydrofuran and 40 mg of sodium hydride is refluxed for 3 hours. The solvent is driven off, the residue is then taken up in ethyl ether and washed with water and the ether phase is then dried over sodium sulfate. It is left to crystallize in a refrigerator for 48 hours and the crystals are filtered off and washed with cyclohexane.

Weight obtained: 200 mg
Melting point: 110° C.
Yield: 33%

EXAMPLE 5

4-(1,2-Dihydro-2-oxopyrid-1-yl)-2,2-dimethyl-6-nitrochromene: SR 45509

A)
trans-4-(1,2-Dihydro-2-oxopyrid-1-yl)-2,2-dimethyl-6-nitrochroman-3-ol

A mixture containing 2.2 g of 2,2-dimethyl-3,4-epoxy-6-nitrochromane and 2 g of 2-hydroxypyridine in 40 ml of tetrahydrofuran is refluxed for 17 hours in the presence of 0.4 ml of benzyltrimethylammonium hydroxide. The solvent is evaporated off and the residue is taken up with ethyl acetate. The organic phase is washed with water; the product crystallizes. It is filtered off, washed with water and crystallized from ethyl acetate to give 800 mg of the expected chromanol.

Melting point: 224-226° C.

B) SR 45509

A solution containing 250 mg of the product obtained in the previous step and 20 mg of sodium hydride in 20 ml of tetrahydrofuran is refluxed for 3 hours. The solvent is evaporated off and the residue is then taken up with a mixture of iced water and ethyl ether. After decantation and washing with water, the organic phase is concentrated and dried over sodium sulfate. The expected product crystallizes from hot isopropyl ether.

Weight obtained: 100 mg
Melting point: 148°-150° C.
Yield: 25.3%

EXAMPLE 6

6-Acetyl-4-(1,2-dihydro-2-oxopyrid-1-yl)-2,2-dimethylchromene SR 45510

A)
trans-6-Acetyl-4-(1,2-dihydro-2-oxopyrid-1-yl)-2,2-dimethylchroman-3-ol

A mixture containing 2.1 g of 6-acetyl-2,2-dimethyl-3,4-epoxychromane and 1.7 g of 2-hydroxypyridine in 40 ml of tetrahydrofuran is refluxed for 16 hours in the presence of 0.4 ml of benzyltrimethylammonium hydroxide. The mixture is cooled and the crystals formed are filtered off and washed with tetrahydrofuran. After drying under vacuum at 60° C., 1.5 g of the expected product are obtained.

Melting point: 260° C.

B) SR 45510

1 g of the product obtained in the previous step, in 40 ml of tetrahydrofuran, is refluxed for 24 hours in the presence of 80 mg of sodium hydride. The mixture is taken up with iced water, the solvent is then evaporated off, extraction is carried out with ethyl ether and the extract is washed with water and dried over sodium sulfate. The solvent is distilled and the product is then purified by chromatography on silica using a methylene chloride/methyl alcohol mixture (99/1, vol/vol) as the eluent.

200 mg of the expected product are obtained.
Melting point: 144°-145° C.
Yield: 21%

Pharmaceutical compositions containing a product according to the invention were prepared.

EXAMPLE 7

Coated tablet

Tablets can be prepared by wet granulation. Ethyl alcohol and purified water are used as auxiliary production solvents. After evaporation of these solvents, magnesium stearate is introduced in an external phase as a lubricant. The tablets are then coated.

| Formulation | |
|---|---|
| SR 44866 | 1 mg |
| 95% ethyl alcohol | 0.02 ml |
| Microcrystalline cellulose | 48 mg |
| Lactose | 69.8 mg |
| Magnesium stearate | 1.2 mg |
| Purified water qs | 120 mg |
| Coating formula: | |
| Methyl hydroxypropyl cellulose 6 cps | 0.14 mg |
| Titanium dioxide | 0.04 mg |
| Polyoxyethylene glycol 6000 | 0.02 mg |
| Purified water | 1.8 mg |
| Talc for film-coated tablets | qs for 122 mg coated tablet |

EXAMPLE 8

| Injectable form | |
|---|---|
| SR 44866 | 1 mg |
| Polyoxyethylene glycol 400 | 0.5 ml |
| Purified water for injectable preparations | qs for 1 ml |

EXAMPLE 9

| Injectable form | |
|---|---|
| SR 44866 | 1 mg |
| Polysorbate 80$^R$ | 0.1 ml |
| Propylene glycol | 0.1 g |
| Purified water for injectable preparations | qs for 1 ml |

The products according to the invention were studied in the in vitro and in vivo pharmacology tests A), B) and C) below.

The following compounds were used as reference compounds:

trans-6-cyano-4-(2-oxopyrrolidin-1-yl)-2,2-dimethylchroman-3-ol:

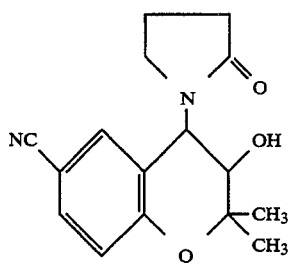

described in European patent 76075 and hereafter referred to as "product A", and 6-cyano-4-(2-oxopyrrolidin-1-yl)-2,2-dimethylchromene, described in European patent application 95535 and hereafter referred to as "product B".

The activity of the products according to the invention was also compared with that of the corresponding chroman-3-ols:

trans-6-cyano-4-(1,2-dihydro-2-oxopyrid-1-yl)-2,2-dimethylchroman-3-ol, prepared in Example 1 (product C), trans-6-bromo-4-(1,2-dihydro-2-oxopyrid-1-yl)-2,2-dimethylchroman-3-ol, prepared in Example 3 (product D), trans-6-chloro-4-(1,2-dihydro-2-oxopyrid-1-yl)-2,2-dimethylchroman-3-ol, prepared in Example 4 (product E), trans-4-(1,2-dihydro-2-oxopyrid-1-yl)-2,2-dimethyl-6-nitrochroman-3-ol, prepared in Example 5 (product F) and trans-6-acetyl-4-(1,2-dihydro-2-oxopyrid-1-yl)-2,2-dimethylchroman-3-ol, prepared in Example 6 (product G).

A) Isolated rat portal vein

Male Sprague Dawley rats (250–300 g) are stunned and then bled after their throats have been cut. The portal vein, ligated in situ at two points 15 mm apart, is isolated, cut longitudinally and then mounted vertically in an experimental cell containing a physiological solution, at 37° C., of the following composition (mmol/1): NaCl:137; KCl:5.4; MgCl$_2$:1.05; CaCl$_2$:18; NaH$_2$PO$_4$:12; NaHCO$_3$:15; glucose: 11.5, into which a mixture of gases containing 95% of oxygen and 5% of carbon dioxide is bubbled.

The vein is subjected to a tension of 500 mg. After a period of stabilization (about 1 h 30 min), the spontaneous contractile activities are recorded with the aid of an isometric sensor. Each measurement is performed successively on 4 preparations.

The product is studied at successive increasing concentrations (15 min per concentration) until the spontaneous contractions have been totally inhibited. The results are expressed in the form of the molar concentrations which causes a 50 per cent inhibition of the spontaneous contractile activities (IC$_{50}$).

The results obtained are collated in Table 1 below.

The results column shows the IC$_{50}$ of the spontaneous contractile activities of isolated rat portal vein.

TABLE 1

| Inhibition of spontaneous contractile activities | | | | |
|---|---|---|---|---|
| | | | Comparison | |
| Product | Example | IC$_{50}$ M | Product | IC$_{50}$ M |
| SR 44866 | 1 | $7.1 \cdot 10^{-9}$ | C | $9.0 \cdot 10^{-8}$ |
| SR 45374 | 3 | $7.9 \cdot 10^{-9}$ | D | $2.5 \cdot 10^{-7}$ |
| SR 45435 | 4 | $8.0 \cdot 10^{-9}$ | E | $1.9 \cdot 10^{-7}$ |
| SR 45509 | 5 | $2.2 \cdot 10^{-9}$ | F | $1.6 \cdot 10^{-8}$ |
| SR 45510 | 6 | $1.1 \cdot 10^{-8}$ | G | $1.9 \cdot 10^{-7}$ |
| A | | $6.8 \cdot 10^{-8}$ | B | $7.0 \cdot 10^{-8}$ |

All the compounds studied have a substantial inhibitory activity against the spontaneous contractions of the vein, which is greater than that of the reference products.

It is found that the activity of each chromene derivative according to the invention is at least 10 times greater than that of the corresponding chroman-3-ol derivative, while the comparison products A and B have similar activities.

B) Guinea-pig papillary muscle

Male Albino Charles River guinea-pigs (300–400 g) are stunned and then bled after their throats have been cut. The heart is isolated and opened and the right papillary muscle is excised and then kept alive in an experimental cell containing a physiological solution at 36° C. (composition described above).

The preparation is stimulated with the aid of a bipolar electrode connected to a stimulator (frequency =60 beats per minute). The ventricular action potential is measured by the conventional microelectrode method. The characteristic parameters were measured on the action potentials (AP) before and after the introduction of the test product at 3 successive increasing concentrations (30 minutes of perfusion per concentration). The concentration which produces a 50 per cent reduction in the duration of the AP is indicated (IC$_{50}$).

The results are reported in Table 2 below:

TABLE 2

| Reduction in the duration of the action potential | | |
|---|---|---|
| Product | Example | IC$_{50}$ |
| SR 44866 | 1 | $1.5 \cdot 10^{-6}$ |
| Product A | — | $1.6 \cdot 10^{-5}$ |
| Product C | — | $2.0 \cdot 10^{-5}$ |

The Table shows that the duration of the action potential is markedly decreased. In particular, the concentration of SR 44866 which produces a 50 per cent reduction in this parameter is 10 times lower than that of product A, demonstrating a greater electrophysiologically activity on the membrane permeability responsible for this repolarization phase.

The electrophysiological profile of the compound studied shows that it has no significant effect on the rest potential and the maximum depolarization rate; this means that the compound studied has no local anesthetic activity.

C) Antihypertensive activity on vigilant spontaneously hypertensive rats (SHR)

The experiment is performed on male SHR (of the Wistar strain) aged between 11 and 12 weeks; under pentobarbital anesthesia, a catheter is implanted in a carotid artery on the day before the experiment. In the experiment, the diastolic pressure (DP) and systolic pressure (SP) of the vigilant animals are recorded continuously 1 hour before and up to 2 hours after administration of the product. The heart rate (HR) is determined from the pulse pressure and recorded continuously for the same time.

The products were administered orally in a volume of 2 ml per 100 g of body weight after suspension in a 5% aqueous solution of gum arabic.

The results are reported in Table 3 below.

TABLE 3

| | | | Decrease in blood pressure | |
|---|---|---|---|---|
| Product | Example | Dose mg/kg p.o. | Maximum decrease in mean blood pressure mm of mercury ($\pm$ s.e.) | Duration of the effect (minutes) |
| SR 44866 | 1 | 0.02 | 34 $\pm$ 6 | 90 |
| | | 0.03 | 41 $\pm$ 6 | >120 |
| SR 45374 | 3 | 0.10 | 32 $\pm$ 6 | >120 |
| SR 45435 | 4 | 0.20 | 70 $\pm$ 8 | >120 |
| Product A | — | 0.10 | 30 $\pm$ 10 | 60 |
| | | 0.20 | 56 $\pm$ 11 | 90 |

The products according to the invention are powerful antihypertensives with an activity of the same order as or greater than that of product A.

Furthermore, it was found that the compounds representative of the present invention have a longer duration of action than product A.

The products of the invention were also studied as antiarrhythmics in test D) below.

D) Antiarrhythmic activity on vigilant dogs

The method used is the one described by Dupuis et al. (Br. J. Pharmacol., 1976, 58, p. 409), in which an acute infarction is caused by the insertion of a copper spiral into the coronary circulation, with the thorax closed off. The ECG is measured by telemetry and the extrasystoles are analyzed and counted automatically While the animal is being monitored by an internal television circuit. The products were administered orally to animals presenting at least 50 per cent of extrasystoles.

A compound representative of the present invention—SR 44866—administered orally at doses of 0.03 mg/kg and 0.1 mg/kg, shows a substantial antiarrhythmic activity by reducing the number of extrasystoles or by restoring a sinus rhythm for a period varying from 45 minutes to 2 hours according to the animals.

The biological data above show that the compounds according to the invention are powerful antihypertensives and potential antiarrhythmics.

The acute toxicity of a product representative of the invention—SR 44866—was measured on a group of 10 mice by oral administration at different doses and compared with that of product A.

The lethal doses (LD) were calculated for the 2 products and are reported in Table 4 below.

TABLE 4

| | $LD_0$ mg/kg | $LD_{50}$ mg/kg |
|---|---|---|
| SR 44866 | 500 | 1000 |
| Product A | 500 | between 500 and 1000 |

Thus the 2 products have a comparable toxicity whereas the activity of SR 44866 is about 10 times greater in the majority of the tests. In conclusion, the products according to the invention have a greater therapeutic index than the reference product.

What is claimed is:

1. 6-cyano-4-(1,2-dihydro-2-oxopyrid-1-yl)-2,2-dimethyl-chromene.

2. A pharmaceutical composition for treating hypertension disorders of smooth muscle contraction and cardiac; said composition having as the active ingredient an effective amount of 2,2-dimethylchromene compound according to claim 1 in combination with a pharmaceutical excipient.

3. A pharmaceutical composition for treating cardiac arrhythmia; said composition having as the active ingredient an effective amount of 2,2-dimethylchromene compound according to claim 1 in combination with a pharmaceutical excipient.

4. A pharmaceutical composition for treating asthma, said composition having as the active ingredient an effective amount of a 2,2-dimethylchromene compound according to claim 1 in combination with a pharmaceutical excipient.

5. A pharmaceutical composition which comprises the 2,2-dimethylchromene compound of claim 1 in combination with a pharmaceutical excipient.

6. A pharmaceutical composition according to claims 2, 3 or 5 which contains from 0.5 to 200 mg. of active ingredient per dosage unit, mixed with a pharmaceutical excipient.

7. A method for treating hypertension which comprises administering to a patient in need thereof an effective amount of the composition according to claim 2.

8. A method for treating cardiac arrhythmia which comprises administering to a patient in need thereof, an effective amount of the composition according to claim 3.

9. A method for treating asthma which comprise administering to a patient in need thereof, an effective amount of the composition according to claim 4.

* * * * *